US010899021B2

(12) United States Patent
Robinson et al.

(10) Patent No.: US 10,899,021 B2
(45) Date of Patent: Jan. 26, 2021

(54) WHEELED CART WITH VIBRATION REDUCTION DEVICE, AND RELATED SYSTEMS AND METHODS

(71) Applicant: INTUITIVE SURGICAL OPERATIONS, INC., Sunnyvale, CA (US)

(72) Inventors: David Robinson, Los Altos, CA (US); Matthew R. Cavalier, San Jose, CA (US); Gregory W. Dachs, San Mateo, CA (US); Michael Hanuschik, Mountain View, CA (US); Jason Jiang, Los Altos, CA (US); Paul W. Mohr, Mountain View, CA (US); Bruce M. Schena, Menlo Park, CA (US); Mark W. Zimmer, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/860,569

(22) Filed: Apr. 28, 2020

(65) Prior Publication Data
US 2020/0254633 A1  Aug. 13, 2020

Related U.S. Application Data

(63) Continuation of application No. 16/577,381, filed on Sep. 20, 2019, now Pat. No. 10,668,633, which is a (Continued)

(51) Int. Cl.
*B25J 19/00* (2006.01)
*A61B 50/13* (2016.01)
(Continued)

(52) U.S. Cl.
CPC .......... *B25J 19/0091* (2013.01); *A61B 34/30* (2016.02); *A61B 34/35* (2016.02); *A61B 34/70* (2016.02);
(Continued)

(58) Field of Classification Search
CPC ....... B25J 19/0091; A63B 34/30; A63B 34/70
See application file for complete search history.

(56) References Cited

U.S. PATENT DOCUMENTS

| 5,642,898 A | * | 7/1997 | Wise | B25H 1/04 |
| | | | | 280/47.19 |
| 10,071,488 B2 | * | 9/2018 | Robinson | A61B 50/13 |

(Continued)

FOREIGN PATENT DOCUMENTS

| CN | 101443162 A | 5/2009 |
| DE | 10161113 A1 | 6/2003 |

(Continued)

OTHER PUBLICATIONS

Extended European Search Report for Application No. EP15765322.1, dated Oct. 20, 2017, 8 pages.

(Continued)

*Primary Examiner* — John D Walters
*Assistant Examiner* — James J Triggs
(74) *Attorney, Agent, or Firm* — Jones Robb, PLLC

(57) ABSTRACT

A surgical cart assembly may comprise a base portion; a plurality of wheels coupled to the base portion; a column extending vertically from the base portion; a manipulator arm coupled to an end portion of the column; a stabilization device coupled to the base portion, the stabilization device moveable between a retracted position and a deployed position; an actuation device to cause movement of the stabilization device between the retracted position and the deployed position; and a biasing element coupled to the (Continued)

stabilization device, the biasing element exerting a biasing force to bias the stabilization device toward the retracted position. The stabilization device may comprise a stabilization surface, the stabilization surface contacting the ground surface on which the surgical cart assembly is supported in the deployed position of the stabilization device, and the stabilization surface spaced from the ground surface in the retracted position of the stabilization device.

20 Claims, 10 Drawing Sheets

Related U.S. Application Data continuation of application No. 16/039,599, filed on Jul. 19, 2018, now Pat. No. 10,464,219, which is a continuation of application No. 15/126,770, filed as application No. PCT/US2015/020911 on Mar. 17, 2015, now Pat. No. 10,071,488.

(60) Provisional application No. 61/954,258, filed on Mar. 17, 2014.

(51) Int. Cl.
| | | |
|---|---|---|
| *A61B 34/30* | (2016.01) | |
| *A61B 34/35* | (2016.01) | |
| *A61B 34/00* | (2016.01) | |
| *B25J 5/00* | (2006.01) | |
| *A61B 17/00* | (2006.01) | |
| *A61B 90/00* | (2016.01) | |
| *B62B 5/04* | (2006.01) | |

(52) U.S. Cl.
CPC .............. *A61B 50/13* (2016.02); *B25J 5/007* (2013.01); *A61B 2017/00539* (2013.01); *A61B 2090/064* (2016.02); *B62B 5/049* (2013.01)

(56) References Cited

U.S. PATENT DOCUMENTS

| | | | |
|---|---|---|---|
| 10,464,219 B2 | 11/2019 | Robinson et al. | |
| 10,668,633 B2 | 6/2020 | Robinson et al. | |
| 2006/0082088 A1 | 4/2006 | Webster et al. | |
| 2007/0142825 A1 | 6/2007 | Prisco et al. | |
| 2007/0163816 A1 | 7/2007 | Schena et al. | |
| 2009/0024142 A1 | 1/2009 | Ruiz | |
| 2009/0085317 A1* | 4/2009 | Livengood | A61M 5/1415 280/79.3 |
| 2010/0137880 A1 | 6/2010 | Nahum et al. | |
| 2013/0325023 A1* | 12/2013 | Sengun | A61B 17/56 606/92 |
| 2013/0325031 A1 | 12/2013 | Schena et al. | |
| 2013/0325033 A1 | 12/2013 | Schena et al. | |
| 2014/0039681 A1 | 2/2014 | Bowling et al. | |
| 2014/0052153 A1 | 2/2014 | Griffiths et al. | |
| 2014/0076659 A1 | 3/2014 | Terry | |
| 2014/0078659 A1* | 3/2014 | Iwaniszczuk | H04M 1/0247 361/679.09 |
| 2014/0297130 A1 | 10/2014 | Griffiths et al. | |
| 2014/0316654 A1* | 10/2014 | Griffiths | A61B 50/18 701/41 |
| 2018/0319023 A1* | 11/2018 | Robinson | B25J 19/0091 |
| 2020/0101629 A1 | 4/2020 | Robinson et al. | |

FOREIGN PATENT DOCUMENTS

| | | |
|---|---|---|
| JP | 2003116876 A | 4/2003 |
| JP | 2010530268 A | 9/2010 |
| JP | 2013233421 A | 11/2013 |
| WO | WO-2009104318 A1 | 8/2009 |
| WO | WO-2015142812 A1 | 9/2015 |
| WO | WO-2016145044 A1 | 9/2016 |

OTHER PUBLICATIONS

International Search Report and Written Opinion for Application No. PCT/US15/20911, dated Jun. 19, 2015, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP20190550.2 dated Oct. 21, 2020, 9 pages.

* cited by examiner

WHEELED CART WITH VIBRATION REDUCTION DEVICE, AND RELATED SYSTEMS AND METHODS

CROSS-REFERENCE TO RELATED APPLICATIONS

This application is a continuation application of U.S. application Ser. No. 16/577,381, filed Sep. 20, 2019, which is a continuation application of U.S. application Ser. No. 16/039,599, filed on Jul. 19, 2018 (now U.S. Pat. No. 10,464,219), which is a continuation application of U.S. application Ser. No. 15/126,770, filed on Sep. 16, 2016 (now U.S. Pat. No. 10,071,488), which is a U.S. national stage application under 35 U.S.C. § 371(c) of International Application No. PCT/US2015/020911, filed on Mar. 17, 2015, which claims the benefit of priority to U.S. Provisional Application No. 61/954,258, filed Mar. 17, 2014, each of which is hereby incorporated by reference in their entirety.

TECHNICAL FIELD

Aspects of the present disclosure relate to wheeled carts that include vibration reduction devices, and related systems and methods.

BACKGROUND

A teleoperated (robotic) surgical system may include a surgeon console at which a surgeon may input commands to control one or more teleoperated surgical instruments mounted to manipulator arms of a patient side cart during a surgical procedure. The patient side cart may be moved about an operating room, such as to position the patient side cart proximate a patient for the surgical procedure. One consideration with such patient side carts is any vibration that could be transmitted to the mounted instruments, such as via the manipulator arms, such as during movement of the patient side cart. While patient side carts have been effective for instrument mounting and minimizing vibrations, further improvements upon patient side carts are desirable. For example, it may be desirable to provide patient side carts with devices to mechanically ground patient side carts and further reduce vibrations.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a patient side cart for a teleoperated surgical system may comprise a base, a column connected to the base, a boom connected to the column, a manipulator arm connected to the boom, and a vibration reduction member. The manipulator arm may be configured to support a surgical instrument. The vibration reduction member may be configured to be moved between deployed and retracted positions relative to the base. The vibration reduction member may engage a ground surface in the deployed position and not be in contact with the ground surface in the retracted position.

In accordance with another exemplary embodiment, a cart may comprise a base, a plurality of wheels connected to the base and configured to transport the cart along a ground surface, and a vibration reduction member. The vibration reduction member may be configured to be moved between deployed and retracted positions relative to the base. The vibration reduction member may be in contact with the ground surface in the deployed position and may be not in contact with the ground surface in the retracted position.

In accordance with another exemplary embodiment, a method of controlling a vibration reduction member of a patient side cart for a teleoperated surgical system may comprise detecting an occurrence of a first event corresponding to preparation of the patient side cart for a surgical procedure. The method may further comprise issuing a command signal to an actuation device to deploy the vibration reduction member to contact a ground surface upon which the patient side cart is located.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
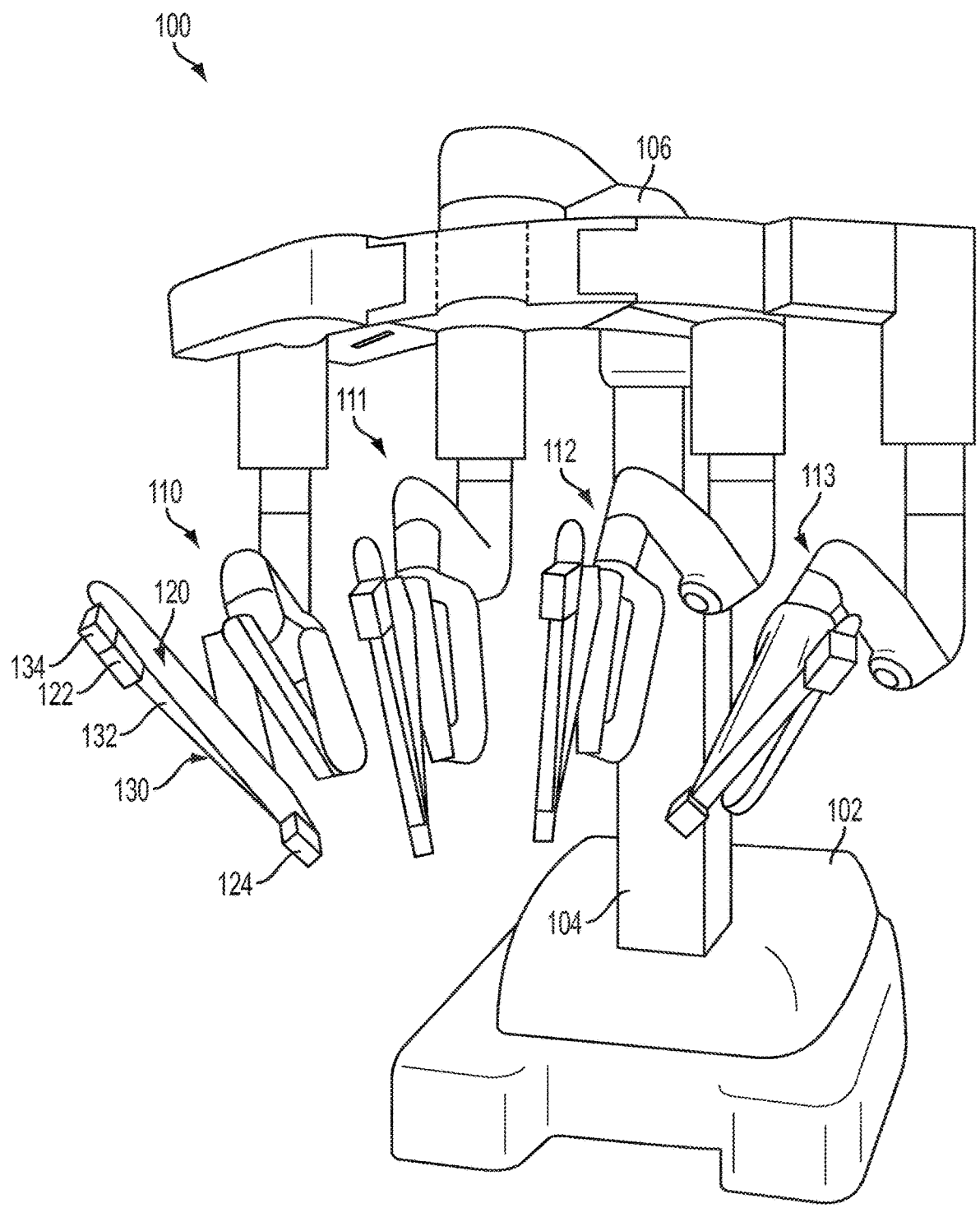
FIG. 1 is a perspective schematic view of a patient side cart, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates patient side carts for teleoperated surgical systems that include features to reduce vibrations in patient side carts. The patient side carts may include systems to facilitate control of the deployment and retraction of the vibration reduction features, such as to automatically deploy and retract vibration reduction features without commands from a user to deploy or retract the vibration reduction features. Thus, the reduction of vibrations in a patient side cart may be facilitated and controlled without requiring a user to actively to deploy or retract the vibration reduction features.

Various exemplary embodiments of the present disclosure contemplate a cart including a vibration reduction device to facilitate reduction of vibrations. The vibration reduction device may include a vibration reduction member configured to be moved between deployed and retracted positions relative to a base of the cart. The cart may be, for example, a patient side cart for a teleoperated surgical system comprising a base, a column connected to the base, a boom connected to the column, and a manipulator arm connected to the boom. The manipulator arm may be configured to support a surgical instrument. The vibration reduction member engages a ground surface in the deployed position and is not in contact with the ground surface in the retracted position. The vibration reduction member may be coupled to the base and may be received in the base in the retracted position. The patient side cart may comprise a plurality of vibration reduction members. The patient side cart may further comprise a biasing device to bias the vibration reduction member to the retracted position. An actuation device may move the vibration reduction member from the retracted position to the deployed position. The actuation device may exert a force to overcome the biasing device. The patient side cart may further comprise a hydraulic pressure system configured to supply hydraulic pressure to the actuation device. The patient side cart may comprise a plurality of vibration reduction members and a plurality of actuation devices to actuate respective vibration reduction members, wherein the hydraulic pressure system comprises a single hydraulic circuit configured to supply the hydraulic pressure to the plurality of actuation devices. The hydraulic pressure system may comprise a sensor configured to monitor the hydraulic pressure. The patient side cart may include a manual release device configured to be manually actuated by a user to release the hydraulic pressure of the hydraulic pressure system. The manual release device may be configured to actuate a release valve of the hydraulic pressure system. The patient side cart may comprise a wheel driven by an electric motor, wherein the electric motor is locked in the deployed position of the vibration reduction member and actuation of the manual release device unlocks the electric motor to permit the wheel to freely rotate. The manual release device may be located in a compartment within the base, with the compartment being closeable by a door, wherein, when the manual release device is in an actuated state, a stop member is positioned to block closing of the door.

In the various exemplary embodiments described herein, the cart may comprise a controller configured to control deployment and retraction of the vibration reduction member. The controller may be configured to automatically deploy the vibration reduction member upon the occurrence of a first event and is configured to automatically retract the vibration reduction member upon the occurrence of a second event. The first event may be mounting a cannula to manipulator arm. The second event may be removal of a cannula mounted to the patient side cart. The cannula for the second event may be a last remaining cannula mounted to the patient side cart during a surgical procedure.

Various exemplary embodiments of the present disclosure also contemplate a method of controlling a vibration reduction member of a patient side cart for a teleoperated surgical system. The method may comprise detecting the occurrence of a first event corresponding to preparation of the patient side cart for a surgical procedure and issuing a command signal to an actuation device to deploy the vibration reduction member to contact a ground surface upon which the patient side cart is located. The first event may comprise mounting a cannula to a manipulator arm of the patient side cart. The method may further comprise detecting the occurrence of a second event corresponding to ending the surgical procedure, and issuing a command signal to the actuation device to retract the vibration reduction member. The second event may be removal of a cannula mounted to the patient side cart. The cannula of the second event may be a last remaining cannula mounted to the patient side cart during a surgical procedure.

Referring now to FIG. 1, an exemplary embodiment of a patient side cart 100 of a teleoperated surgical system is shown. As those having ordinary skill in the art are familiar with, a teleoperated surgical system may further include a surgeon console (not shown) for receiving input from a user to control instruments of patient side cart 100, as well as an auxiliary control/vision cart (not shown), as described in for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. By way of non-limiting example, a teleoperated surgical system of the type contemplated by the present disclosure includes one of the da Vinci.®. Surgical Systems available from Intuitive Surgical, Inc.

Patient side cart 100 may include a base 102, a main column 104, and a main boom 106 connected to main column 104. Patient side cart 100 also may include a plurality of manipulator arms 110, 111, 112, 113, which may each be connected to main boom 106. Portions of manipulator arms 110, 111, 112, 113 may include an instrument mount portion 120 to which an instrument 130 may be mounted, as illustrated for manipulator arm 110. Manipulator arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 may comprise an actuation interface assembly 122 and a cannula mount 124, with a shaft 132 of instrument 130 extending through cannula mount 124 (and on to a surgery site during a surgical procedure) and a force transmission mechanism 134 of instrument connecting with the actuation interface assembly 122, according to an exemplary embodiment. Cannula mount 124 may be configured to hold a cannula (not shown) through which shaft 132 of instrument 130 may extend to a surgery site during a surgical procedure. Actuation interface assembly 122 may contain a variety of mechanisms that are controlled to respond to input commands at the surgeon console and transmit forces to the force transmission mechanism 134 to actuate instrument 130.

Although the exemplary embodiment of FIG. 1 shows an instrument 130 attached to only manipulator arm 110 for ease of viewing, an instrument may be attached to any and each of manipulator arms 110, 111, 112, 113. An instrument 130 may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site. In the exemplary of FIG. 1, either a surgical instrument with an end effector or a camera instrument may be attached to and used with any of manipulator arms 110, 111, 112, 113. However, the embodiments described herein are not limited to the exemplary embodiment of FIG. 1 and various other teleoperated surgical system configurations may be used with the exemplary embodiments described herein.

Figure 2:
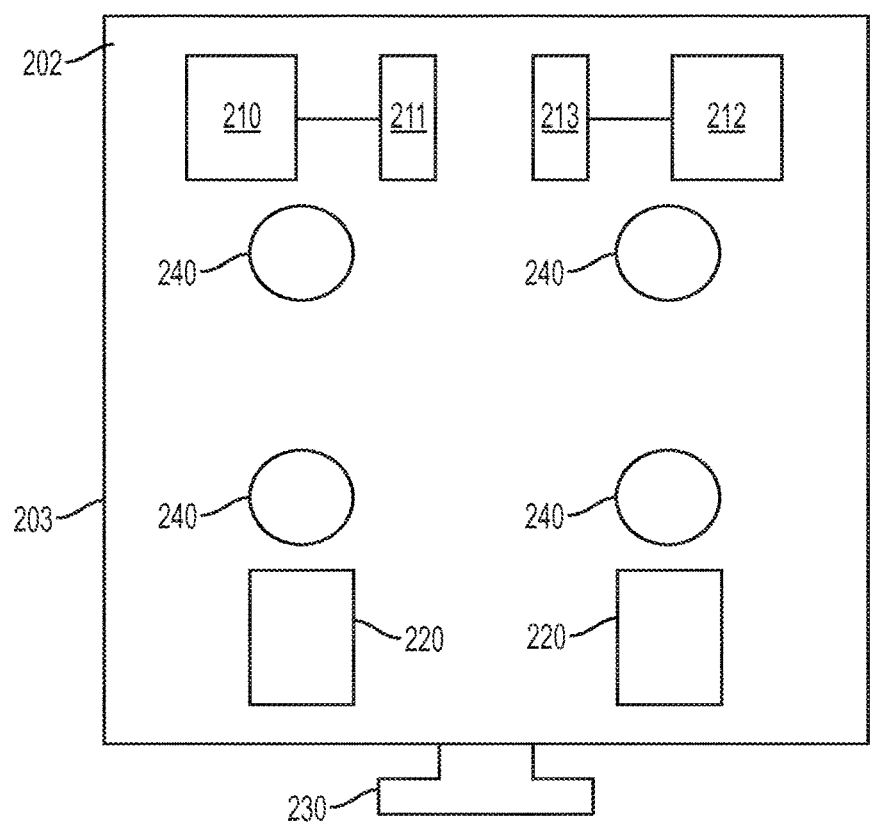
FIG. 2 is a plan schematic view of an exemplary embodiment of a base of a patient side cart including a vibration reduction member.

A patient side cart may include one or more device(s) to control movement of the patient side cart from one location to another, such as when moving the patient side cart about an operating room to prepare for a surgical procedure or after a surgical procedure has been completed. Turning to FIG. 2, a base 202 of a patient side cart (such as patient side cart 100 of the exemplary embodiment of FIG. 1) is schematically shown. Base 202 may include a plurality of wheels to permit movement of a patient side cart from one location to another. According to an exemplary embodiment, one or more of the wheels may be driven to move the patient side cart. As shown in the exemplary embodiment of FIG. 2, base 202 may include a first wheel 210 driven by a motor 211 and a second wheel 212 driven by a motor 213. Base 202 may further include non-driven wheels 220, which may be, for example, caster wheels that freely move, according to an exemplary embodiment.

The patient side cart including base 202 may include a drive system to maneuver the patient side cart, as described in U.S. application Ser. No. 14/209,239 entitled "Surgical Patient Side Cart with Drive System and Method of Moving a Patient Side Cart," filed on Mar. 13, 2013, now published as U.S. App. Pub. No. US 2014/0297130 A1, published Oct. 2, 2014, which is hereby incorporated by reference in its entirety. As shown in the exemplary embodiment of FIG. 2, base 202 may include two driven wheels 210 and 212 and two non-driven wheels 220 but the various exemplary embodiments described herein are not limited to this arrangement and may include other numbers of driven and non-driven wheels. Nor is a patient side cart in accordance with the present disclosure limited to including a motorized drive control system as set forth in U.S. App. Pub. No. US 2014/0297130 A1, which claims priority to U.S. Provisional Application No. 61/895,249.

The patient side cart including base 202 may include a steering interface 230 for a user to drive the patient side cart from one location to another, according to an exemplary embodiment. Steering interface 230 may be configured, for example, according to the various exemplary embodiments described in U.S. application Ser. No. 14/208,663 entitled "Surgical Patient Side Cart with Steering Interface," filed on Mar. 13, 2014, and now published as U.S. App. Pub. No. US 2014/0316654 A1, published Oct. 23, 2014, which is hereby incorporated by reference in its entirety.

During a surgical procedure, vibration may occur within a patient side cart, such as when components of the patient side cart are actuated and moved. The vibrations may be transmitted through the patient side cart to surgical instruments mounted to manipulator arms of the patient side cart, which may cause the surgical instruments to move to a degree. To address this, a patient side cart may include one or more vibration reduction members to reduce or minimize vibrations in the patient side cart. As shown in the exemplary embodiment of FIG. 2, base 202 may include a plurality of vibration reduction members 240. Vibration reduction members 240 may be configured to contact a ground surface beneath base 202, as will be discussed below, to reduce or minimize vibrations, such as vibrations that occur during movement of a patient side cart, and thus facilitate stabilization of surgical instruments mounted to the patient side cart. The base of a patient side cart may include four vibration reduction members 240, as shown in the exemplary embodiment of FIG. 2, but the various exemplary embodiments described herein are not limited to four vibration reduction members and may instead include other numbers of vibration reduction members, such as, for example, one, two, three, five, six, or more vibration reduction members.

According to an exemplary embodiment, vibration reduction members of a patient side cart need not be used to affect the stability of the patient side cart in terms of minimizing or preventing the patient side cart from tipping or rolling over. Instead, the vibration reduction members may be used to reduce vibrations in the patient side cart, which may in turn lead to movement of surgical instruments mounted to the patient side cart. In view of this, vibration reduction members may be configured to contact a ground surface, but not to do so with sufficient force to lift or otherwise move a patient side cart.

Figure 3:
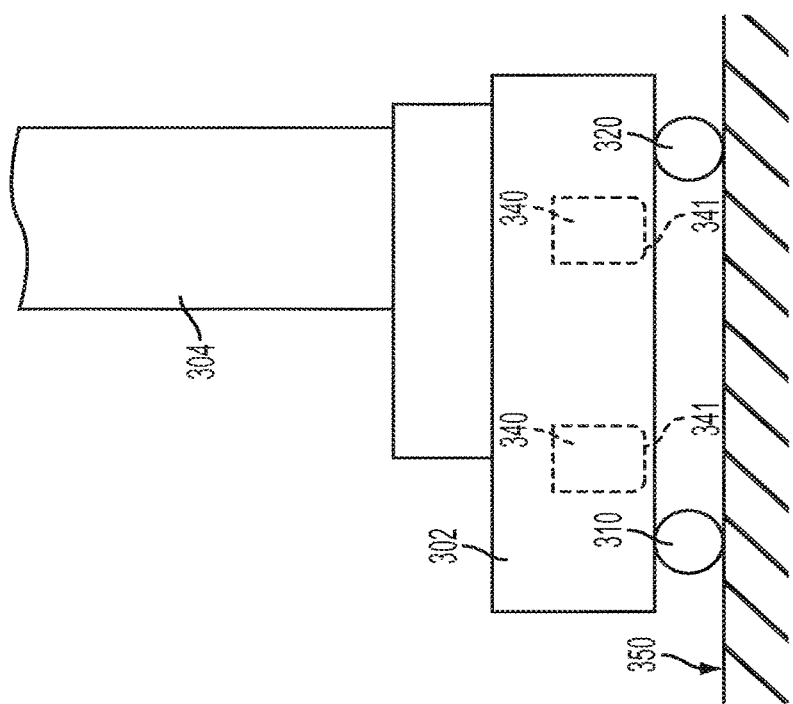
FIG. 3 is a schematic side view of a portion of a patient side cart with a vibration reduction member in a retracted state, according to an exemplary embodiment.

As discussed above, the vibration reduction members of a patient side cart may be configured to contact a ground surface to minimize or reduce vibrations. To facilitate maneuvering of a patient side cart from one location to another, the vibration reduction members may be retractable and deployable. Turning to FIG. 3, a side view is shown of a base 302 and a portion of main column 304 of a patient side cart, which may be arranged according to the exemplary embodiments of FIGS. 1 and 2. For instance, base 302 may include one or more driven wheels 310 and one or more non-driven wheels 320, as discussed above in regard to the exemplary embodiment of FIG. 2. To address vibrations in a patient side cart including base 302, base 302 may include one or more vibration reduction members 340, which are in a retracted state in the exemplary embodiment of FIG. 3, with vibration reduction members 340 not in contact with a ground surface 350 to facilitate maneuvering of the patient side cart.

Figure 4:
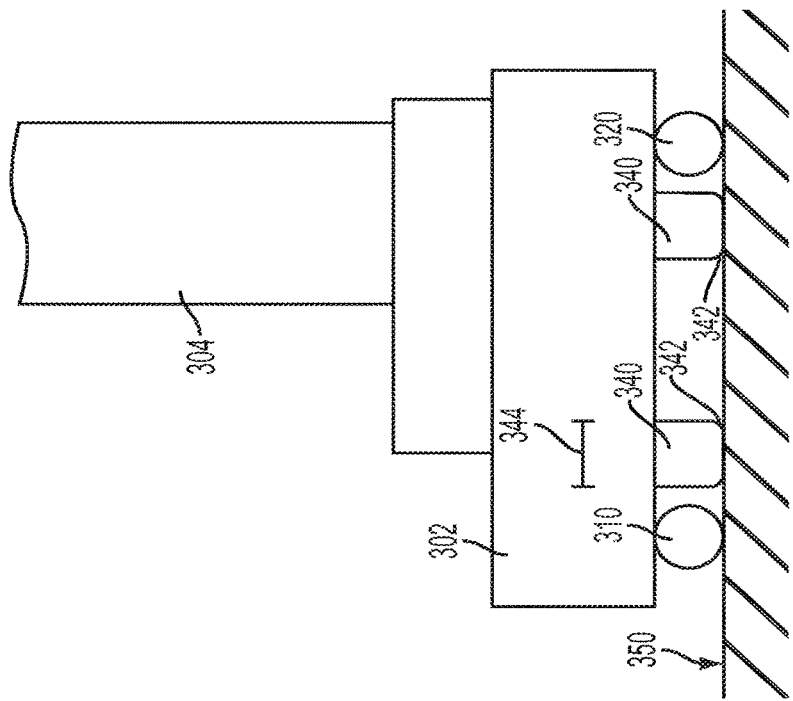
FIG. 4 shows the patient side cart portion of FIG. 3 with the vibration reduction member in a deployed state.

Vibration reduction members 340 may be deployed to contact ground surface 350, as shown in the exemplary embodiment of FIG. 4. Thus, vibration reduction members 340 may be deployed or retracted between respective raised and lowered positions with respect to base 302 and the ground 350, as shown in the exemplary embodiment of FIGS. 3 and 4. For instance, once a patient side cart has been positioned for a surgical procedure, vibration reduction members 340 may be deployed to minimize vibration. According to an exemplary embodiment, a patient side cart may include a controller to control the deployment and retraction of vibration reduction members 340, which may occur when the controller receives information about a status of the patient side cart, as will be discussed in further detail below.

Vibration reduction members may be configured to minimize or reduce vibrations of a patient side cart and in view of additional considerations. Bottom surfaces 341 of vibration reduction members 340 may be substantially flat, according to an exemplary embodiment, such as to maximize contact area between vibration reduction members 340 and ground surface 350. According to an exemplary embodiment, an edge 342 of bottom surface 341 may be rounded, such as to minimize or eliminate marking of ground surface 350 with vibration reduction members 340. As shown in the exemplary embodiment of FIG. 2, vibration reduction members 240, 340 may have a cylindrical shape, although the vibration reduction members of the various exemplary embodiments described herein may have other shapes, such as, for example, a square shape cross-section, rectangular shape cross-section, or other shapes familiar to one of ordinary skill in the art. Vibration reduction members 340 may have a diameter or width 344 ranging, for example, from about 1 inch to about 3 inches, for example from about 1.5 inches to about 2 inches. Vibration reduction members 340 may be configured to fully retract within base 302, such as to maximize an amount of clearance between base 302 and ground surface 350. The vibration reduction members of a patient side cart may also be located within a base of the patient side cart to minimize or eliminate interaction with a user. For example, as shown in the exemplary embodiment of FIG. 2, vibration reduction members 240 may be located away from an outer edge 203 of base 202 to minimize or eliminate vibration reduction members 240 being deployed onto a person's foot. Vibration reduction members 240 may also be positioned within base 202 to facilitate reduction of vibrations, such as closer to a periphery of base 202, according to an exemplary embodiment. Thus, positions of vibration reduction members 240 may be selected in view of these considerations.

Figure 5:
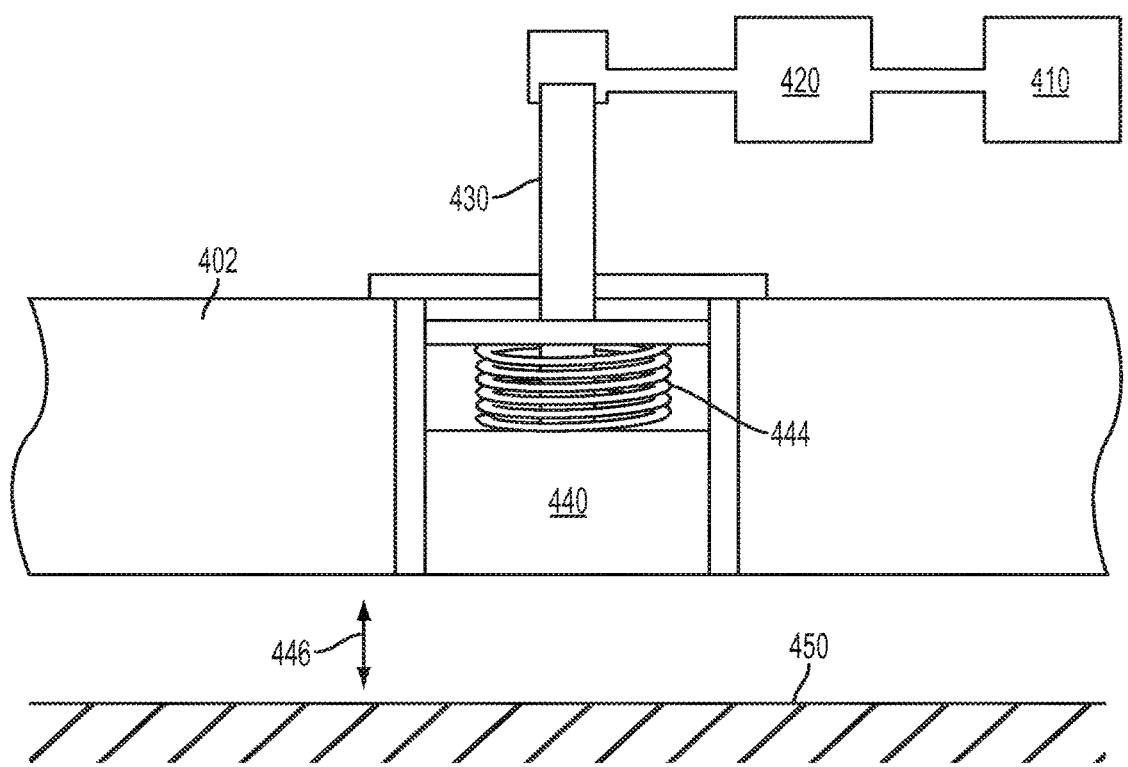
FIG. 5 shows a schematic partial sectional view of an actuation device for a vibration reduction member, according to an exemplary embodiment.

Vibration reduction members may be biased to a retracted position to facilitate retraction of vibration reduction members, such as when a patient side cart is to be moved from one location to another, according to an exemplary embodiment. Turning to FIG. 5, a partial side view is shown of a vibration reduction member 440 in a base 402 of a patient side cart. Vibration reduction member 440 may be used, for example as vibration reduction members 240 and 340 in the exemplary embodiments of FIGS. 2-4. A biasing device may be provided to bias vibration reduction member 440 to a retracted position, such as upward along direction 446 away from a ground surface 450 in the exemplary embodiment of FIG. 5. A biasing device may be, for example, a spring 444 that provides a biasing force to bias vibration reduction member 440 to the retracted position. Although the exemplary embodiment of FIG. 5 depicts a single biasing device (e.g., spring 444) for vibration reduction member 440, the various exemplary embodiments described herein may include other numbers of biasing devices, such as, for example, two, three, four, or more biasing devices.

Further, other biasing devices other than spring 444 that are familiar to one of ordinary skill in the art may be used in the various exemplary embodiments described herein. For example, piston-cylinder device 430 in FIG. 5 is configured to provide hydraulic pressure on either side of a piston (not shown), such as via a double piston-cylinder arrangement. With such an arrangement, vibration reduction member 440 can be deployed downward along direction 446 toward ground surface 450 by applying hydraulic pressure on one side of the piston and can be retracted along direction 446 away from ground surface 450 by applying hydraulic pressure on another side of the piston.

A vibration reduction member may include an actuation device to deploy the vibration reduction member. When a vibration reduction member includes a biasing device, such as spring 444, the deployment device may be configured to overcome the force applied by the biasing device so the vibration reduction member may be moved to the deployed position. According to an exemplary embodiment, a hydraulic pressure system may be used to overcome the force applied by a biasing device and deploy a vibration reduction member. The hydraulic pressure system may include, for example, a pump to supply hydraulic fluid to an actuator for a vibration reduction member, with the pressure of the hydraulic fluid supplied to the actuator overcoming the biasing force and deploying the vibration reduction member. As shown in the exemplary embodiment of FIG. 5, pump 410 may be provided to supply hydraulic pressure to a piston-cylinder device 430, which functions as an actuator for vibration reduction member 440. As pump 410 supplies hydraulic fluid to piston-cylinder device 430, the pressure of the hydraulic fluid causes piston-cylinder device 430 to overcome the force provided by spring 444, which results in vibration reduction member 440 being deployed, such as downward along direction 446 so vibration reduction member 440 contacts ground surface 450. Thus, a controller (not shown in FIG. 5) to control the deployment and retraction of vibration reduction member 440 may issue commands to pump 410 to cause vibration reduction member 440 to be deployed.

To retract a vibration reduction member, an actuation device configured to deploy a vibration reduction member may be deactivated, or the force provided by the device otherwise ceased, to permit retraction of the vibration reduction member, according to an exemplary embodiment. When a biasing device is used to retract a vibration reduction member, deactivation of the deployment device may permit the biasing device to return the vibration reduction member to its retracted position. In the exemplary embodiment of FIG. 5, the hydraulic pressure system may further comprise a release valve 420 to release the pressure supplied to piston-cylinder device 430, permitting spring 444 to move vibration reduction member 440 along direction 446 to its retracted position. According to an exemplary embodiment, release valve 420 may be actuated by the controller configured to control the deployment and retraction of vibration reduction member 440 so the deployment and actuation of vibration reduction member 440 may be actuated by the controller. Release valve 420 may also be manually actuated by a user, such as when vibration reduction member 440 needs to be retracted to facilitate movement of a patient side cart, according to an exemplary embodiment. According to another exemplary embodiment, an actuation device configured to deploy a vibration reduction member may be actuated to retract a vibration reduction member, such as by reducing the force applied to the vibration reduction member by the actuation device, instead of deactivating the actuation device or ceasing the force applied by the actuation device.

Figure 6:
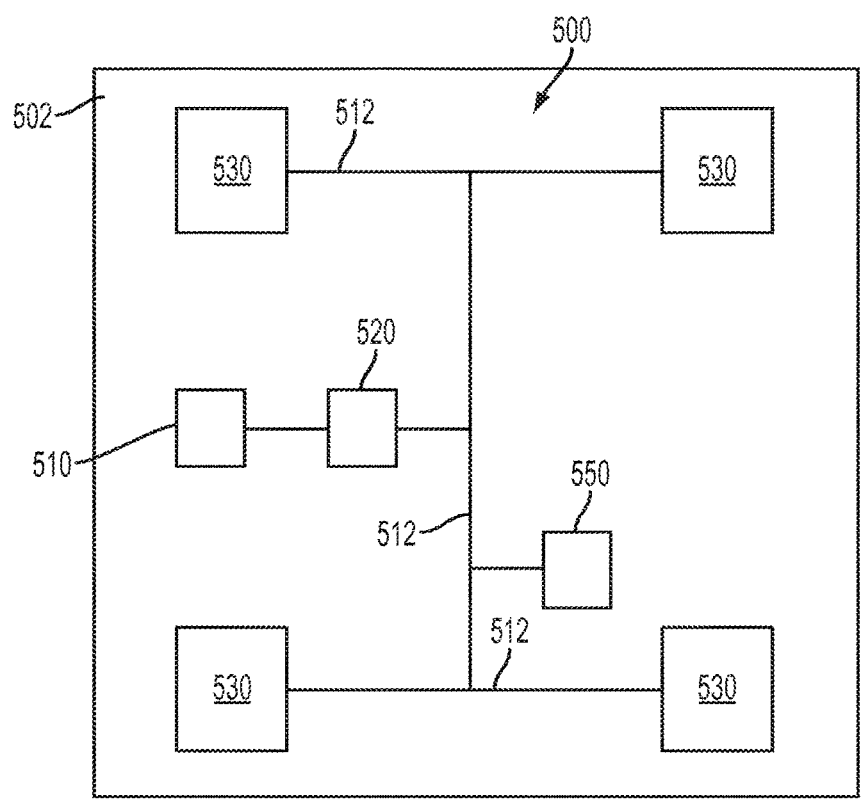
FIG. 6 is a plan schematic view of a hydraulic pressure system for a vibration reduction member, according to an exemplary embodiment.

As discussed above, a hydraulic pressure system may be provided to actuate deployment of the one or more vibration reduction members of a patient side cart. According to an exemplary embodiment, a single hydraulic circuit may be used for all of the vibration reduction members of a patient side cart. Turning to FIG. 6, a hydraulic pressure system 500 is schematically shown in a base 502 of a patient side cart. Hydraulic pressure system 500 may be used for the vibration reduction members of the exemplary embodiments of FIGS. 2-5 described above. As shown in the exemplary embodiment of FIG. 6, hydraulic pressure system 500 may comprise a pump 510 and a release valve 520 (which may be configured according to pump 410 and release valve 410 of the exemplary embodiment of FIG. 5) connected to a hydraulic circuit 512. Hydraulic circuit 512 may be, for example, a single hydraulic circuit connected to every actuator 530 (e.g., piston-cylinder device 430 of the exemplary embodiment of FIG. 4, or other vibration reduction member actuator) for respective vibration reduction members. Thus, a single pump 510 and release valve 520 may be used to actuate every vibration reduction member of a patient side cart. By connecting the actuators 530 for each vibration reduction member with a single hydraulic circuit 512, a force equalization effect for the vibration reduction members can be achieved when the vibration reduction members are deployed to contact a ground surface because each actuator 530 is subjected to substantially the same hydraulic pressure from hydraulic circuit 512.

Various exemplary embodiments may include a single hydraulic circuit, as discussed above in regard to the exemplary embodiment of FIG. 6. However, the various exemplary embodiments described herein are not limited to a single hydraulic circuit and may include a plurality of hydraulic circuits. For example, a base of a patient side cart may include a first hydraulic circuit for the front wheels of the cart and a second hydraulic circuit for the rear wheels of the cart. In another example, a base of a patient side cart may include a separate hydraulic circuit for each vibration reduction member of the base.

A hydraulic pressure system may include a sensor to monitor the hydraulic pressure of the system. As shown in the exemplary embodiment of FIG. 6, hydraulic pressure system 500 may include a regulation device 550 connected to hydraulic circuit 512 to regulate the hydraulic pressure of hydraulic circuit 512. Regulation device 550 may be, for example, a switch connected to pump 510 that deactivates pump 510 once a predetermined pressure has been reached, according to an exemplary embodiment. In another exemplary embodiment, regulation device 550 may be a sensor to monitor the hydraulic pressure and signal pump 510 to deactivate when a predetermined maximum pressure has been reached or determine if a leak has occurred, as manifested by a loss of hydraulic pressure. When this occurs, the controller to control the deployment and retraction of vibration reduction members may provide a notification to a user of a patient side cart, such as a visual and/or audio notification, although other types of notifications are contemplated without departing from the scope of the present disclosure.

According to an exemplary embodiment, hydraulic circuit 512 may include a device to control the pressure of hydraulic circuit 512 should regulation device 550 not function properly. For instance, a device may prevent the hydraulic pressure from exceeding a predetermined maximum hydraulic pressure so hydraulic pressure system 500 does not supply excessive pressure to actuators 530, which could lead to vibration reduction members moving or even lifting a patient side cart. Such a device may be, for example, a relief valve (not shown in FIG. 6) that automatically releases hydraulic pressure when the predetermined maximum hydraulic pressure for the relief valve has been attained, such as when regulation device 550 is not functioning properly.

Although exemplary embodiments have been described above as including a hydraulic pressure system as a device to actuate deployment of vibration reduction members, other devices and systems may be used in the various exemplary embodiments described herein to deploy vibration reduction members. For example, electric motors and other actuators familiar to one of ordinary skill in the art may be used to deploy vibration reduction members in the various exemplary embodiments described herein.

As discussed above with regard to the exemplary embodiments of FIGS. 2-6, a patient side cart may include a controller to control the deployment and retraction of vibration reduction members. Such a system may be useful to automatically deploy and retract vibration reduction members because a user may forget to deploy the vibration reduction members for a surgical procedure to reduce vibrations or forget to retract the vibration reduction members to facilitate movement of the cart, such as once a surgical procedure has been completed. Automatic deployment of the vibration reduction members of a patient side cart may be actuated by the controller, for example, when a first event has occurred and automatic retraction of the vibration reduction members may be actuated by the controller, for example, when a second event has occurred, according to an exemplary embodiment.

According to an exemplary embodiment, a controller to control the deployment and retraction of a vibration reduction member may receive a signal from a sensor monitoring the retraction/deployment state of the vibration reduction member. The sensor may be, for example, a pressure sensor connected to a hydraulic circuit, such as hydraulic circuit 512, of the actuation device for the vibration reduction member that detects when a pressure of the circuit is high, which indicates deployment of the vibration reduction member. In another example, the sensor may be a position sensor that directly detects the movement and/or position of a vibration reduction member. In another example, the sensor may be a contact sensor located on a bottom surface of a vibration reduction member so that when the vibration reduction member contacts a ground surface the sensor is activated and issues a signal to the controller.

Because it may be desirable to deploy vibration reduction members when a patient side cart is ready or nearly ready for a surgical procedure and to retract the vibration reduction members when the surgical procedure has finished, the first and second events may be related to preparing the patient side cart before and after the surgical procedure. According to an exemplary embodiment, the first event to trigger automatic deployment of the one or more vibration reduction members of a patient side cart by the controller may be, for example, mounting a cannula to a manipulator arm of the patient side cart, such as by mounting a cannula (not shown) to cannula mount 124 of manipulator arm 110 (or any of manipulator arms 110-113) in the exemplary embodiment of FIG. 1. Cannula mounts 124 in manipulator arms 110-113 may include one or more sensors to detect the type and/or presence of a cannula mounted to a respective cannula mount of a manipulator arm. For example, a signal from a sensor used to identify what type of cannula has been mounted to a manipulator arm can be used to detect the presence of a cannula mounted to a respective arm. Such a sensor is, for example, a sensor as described in International PCT Application No. PCT/US2015/020913 (now published as WO 2015/142812), filed on a date even herewith and claiming priority to U.S. Provisional Application No. 61/954,318 (entitled "Surgical Cannulas and Related Systems and Methods of Identifying Surgical Cannulas"), filed on Mar. 17, 2014, each of which is hereby incorporated by reference in its entirety.

According to another exemplary embodiment, a sensor to detect the presence of a cannula mounted to a respective arm can be configured as a latch position sensor. A latch position sensor can be configured to detect when a latch used to mount a cannula has been actuated, such as by detecting movement of one or more components of the latch. One example of a suitable sensor that can be used to detect such movement includes a photo-interrupt sensor, although those having ordinary skill in the art would appreciate various other types of sensors that could be used to detect movement of the latch.

According to an exemplary embodiment, a plurality of sensors may be used to detect the presence of a cannula mounted to a respective arm, such as to avoid a false positive reading that could lead to unintended deployment the one or more vibration reduction members. For example, a controller may be configured to deploy the one or more vibration reduction members when signals have been received from more than one cannula presence sensor, such as, for example, from both the cannula presence/identification sensor and the latch position sensor.

Output from one or more sensors used to detect the presence of a cannula may be provided to the controller controlling the deployment and retraction of vibration reduction member(s) so the controller may determine when a cannula has been first mounted to a manipulator arm and the vibration reduction members should be deployed. The second event to trigger automatic retraction of the one or more vibration reduction members of a patient side cart by the controller may be, for example, removing the last cannula mounted to the manipulator arms of the patient side cart. For instance, the controller may receive signals from the sensors of cannula mounts 124 of the various manipulator arms 110-113, determine that only one cannula remains mounted to arms 110-113, and then automatically retract the vibration reduction members when the last cannula has been removed, which may represent that the patient side cart is ready or nearly ready to be moved after finishing a surgical procedure.

Although the various exemplary embodiments described herein may include a controller that automatically deploys and retracts vibration reduction member(s) according to the first and second events described above, other events may be used for the first and second events. For example, the first event could be the occurrence of mounting a second cannula to the manipulator arms of a patient side cart, the occurrence of mounting a third cannula, or other event. According to another exemplary embodiment, an event could be the actuation or release of a dead man switch in the steering interface 230 of FIG. 2. Exemplary embodiments of dead man switches are described in U.S. App. Pub. No. US 2014/0316654 A1, published Oct. 23, 2014, which claims priority to U.S. Provisional Application No. 61/791,924, filed Mar. 15, 2013, each of which is incorporated by reference herein. Release of a dead man switch in steering interface 230 may represent that movement of the patient side cart is finished and the cart will be prepared for a surgical procedure. Thus, the controller may deploy vibration reduction member(s) when this event occurs. Similarly, actuation of the dead man switch may represent that a surgical procedure has finished and the patient side cart is ready for movement. Thus, the controller may retract the vibration reduction member(s).

According to an exemplary embodiment, the controller to control the deployment and retraction of the vibration reduction member(s) of a patient side cart may retract the vibration reduction member(s) in two stages to facilitate movement of the patient side cart in a short time period. In a first stage, vibration reduction member(s) may be retracted from a ground surface by the controller. The first stage may occur, for example, in about one second or less. In a second stage, the vibration reduction member(s) may continue to be retracted to a fully retracted position but movement of the patient side cart may be permitted because although the vibration reduction member(s) are still being retracted, the vibration reduction member(s) are no longer in contact with the ground surface.

During use of a patient side cart, it is possible for a system error to occur that may be cleared by a user. One method of clearing an error is to power cycle the patient side cart. According to an exemplary embodiment, when such a power cycle occurs, the controller to control deployment and retraction of the vibration reduction member(s) of the patient side cart may be configured to maintain the vibration reduction member(s) in a deployed position so the vibration reduction member(s) remain in contact with a ground surface during the power cycle so the vibration reduction member(s) may facilitate reduction of vibration even during the power cycle. The controller may be configured in this way by receiving signals, for example, from the sensors of cannula mounts indicating that cannulas are still mounted and also receiving notification that a user has commanded the power cycle, according to an exemplary embodiment.

Figure 7:
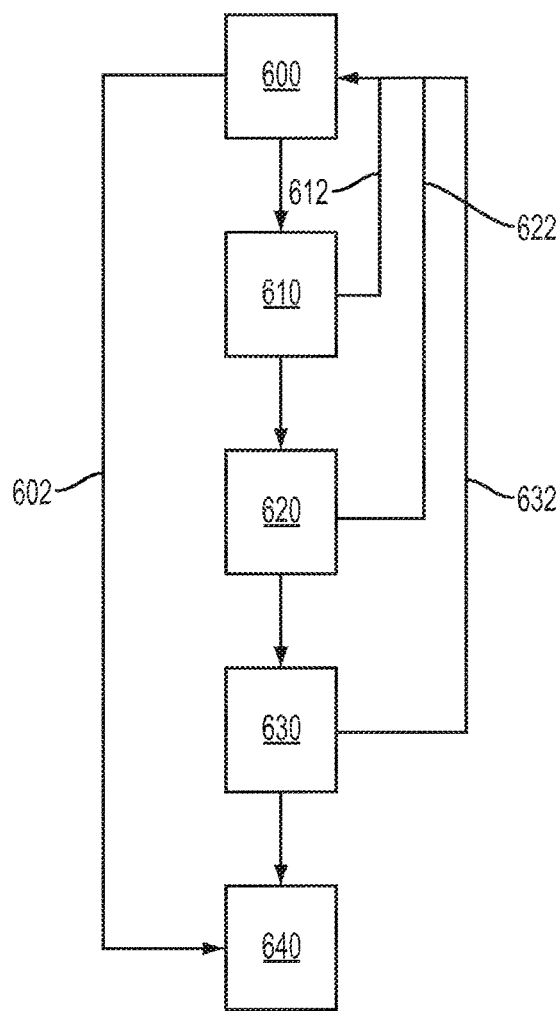
FIG. 7 depicts a schematic method for deploying a vibration reduction member, according to an exemplary embodiment.

Turning to FIG. 7, a schematic flowchart is provided for an exemplary embodiment of controlling the vibration reduction member(s) of a patient side cart to be deployed. The various exemplary embodiments of vibration reduction members described herein may be deployed, such as via the controller to control deployment and retraction, according to the exemplary embodiment of FIG. 7. In a first step 600, the vibration reduction member(s) are in a retracted position. The control process proceeds to step 610, in which a command is provided, such as via the controller, to deploy the vibration reduction member(s). When a deployment device for the vibration reduction member(s) includes the hydraulic pressure system described above with regard to the exemplary embodiments of FIGS. 2-6, the pressure of the hydraulic pressure system may be low in the state of step 610. In step 610, the deployment may commence by actuating a pump of the hydraulic pressure system, such as pump 410 or 510 of the exemplary embodiments of FIGS. 5 and 6. According to an exemplary embodiment, the controller may monitor the pump, such as to determine whether the pump is receiving power. If the pump is not receiving power within a predetermined time, the process may return to step 600, as shown by step 618 in FIG. 7.

When the pump is receiving power, the process proceeds to step 620, in which the pump is actuated. According to an exemplary embodiment, the controller may monitor the pump and/or hydraulic circuit to determine whether the pressure is increasing. If the pressure does not increase within a predetermined time, the process may return to step 600, such as via step 622 in FIG. 7. When the pressure is increasing, the process proceeds to step 630, in which a desired pressure has been attained and the controller issues a command to cease power to the pump. If the power to the pump is not deactivated within a predetermined time, the controller may command a release valve, such as release valve 420 or 520 of FIGS. 5 and 6, to open to release the hydraulic pressure and return the process to step 600, such as via step 632 in FIG. 7. Once the power to the pump has been successfully deactivated, the process may finish at step 640, in which the vibration reduction member(s) have been deployed. The deployment process may follow a different route than described above, according to an exemplary embodiment. For example, the process may proceed along step 602 from step 600 to step 640, such as when the hydraulic system is already at a high pressure and a command to deploy the vibration reduction member(s) is the only step required.

According to an exemplary embodiment, when the vibration reduction member(s) of a patient side cart have been deployed, the driven wheels of the patient side cart may also be locked, such as to facilitate immobilization of the patient side cart during a surgical procedure. For example, locks within motors 211 and 213 for driven wheels 210 and 212 of the exemplary embodiment of FIG. 2 may be engaged when the vibration reduction member(s) of a patient side cart have been deployed.

Figure 8:
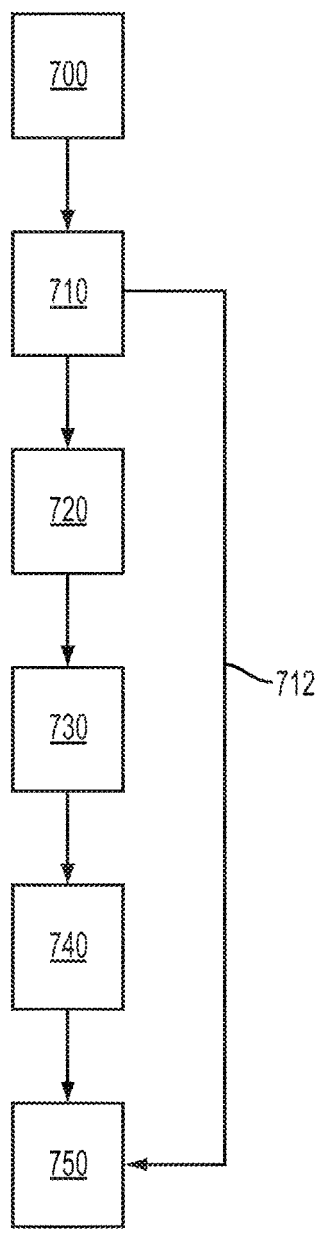
FIG. 8 depicts a schematic method for retracting a vibration reduction member, according to an exemplary embodiment.

Turning to FIG. 8, a schematic flowchart is provided for an exemplary embodiment of controlling the vibration reduction member(s) of a patient side cart to be retracted. The various exemplary embodiments of vibration reduction members described herein may be retracted, such as via the controller to control deployment and retraction, according to the exemplary embodiment of FIG. 8. In a first step 700, the vibration reduction member(s) are in a deployed position. The control process proceeds to step 710, in which a command is provided, such as via the controller, to retract the vibration reduction member(s). According to an exemplary embodiment, a release valve, such as release valve 420 or 520 of FIGS. 5 and 6, is actuated to release hydraulic pressure within the hydraulic pressure system. As a result, a biasing device, such as spring 444 in FIG. 5, may apply a biasing force to move the vibration reduction member(s) to the retracted position.

The process of FIG. 8 may proceed to step 720, in which the vibration reduction member(s) begin to retract. Step 720 may be, for example, the first stage of deployment discussed above in which the vibration reduction member(s) begin to retract. The process may proceed to step 730, in which the vibration reduction member(s) are partially retracted, such as, for example, in about one second or less between step 720 and step 730, which permits the patient side cart to be moved while the vibration reduction member(s) continue to retract. The process proceeds to step 740, in which power is deactivated to the release valve, permitting the release valve to close in preparation for the next deployment of the vibration reduction member(s). Finally, in step 750, the vibration reduction member(s) may be in a fully retracted state. According to an exemplary embodiment, the controller may monitor the status of the release valve and proceed directly to step 750 from step 710, such as via step 712, if the power actuating the release valve is not ceased within a predetermined time. Although the exemplary embodiment of FIG. 8 has been discussed with regard to retracting a vibration reduction member by actuating a release valve, the various exemplary embodiments described herein may use other methods of retracting a vibration reduction member, such as, for example, actuating an actuation device (e.g., hydraulic pressure circuit) to reduce the force applied by the actuation device instead of ceasing the force or deactivating the actuation device.

Figure 9:
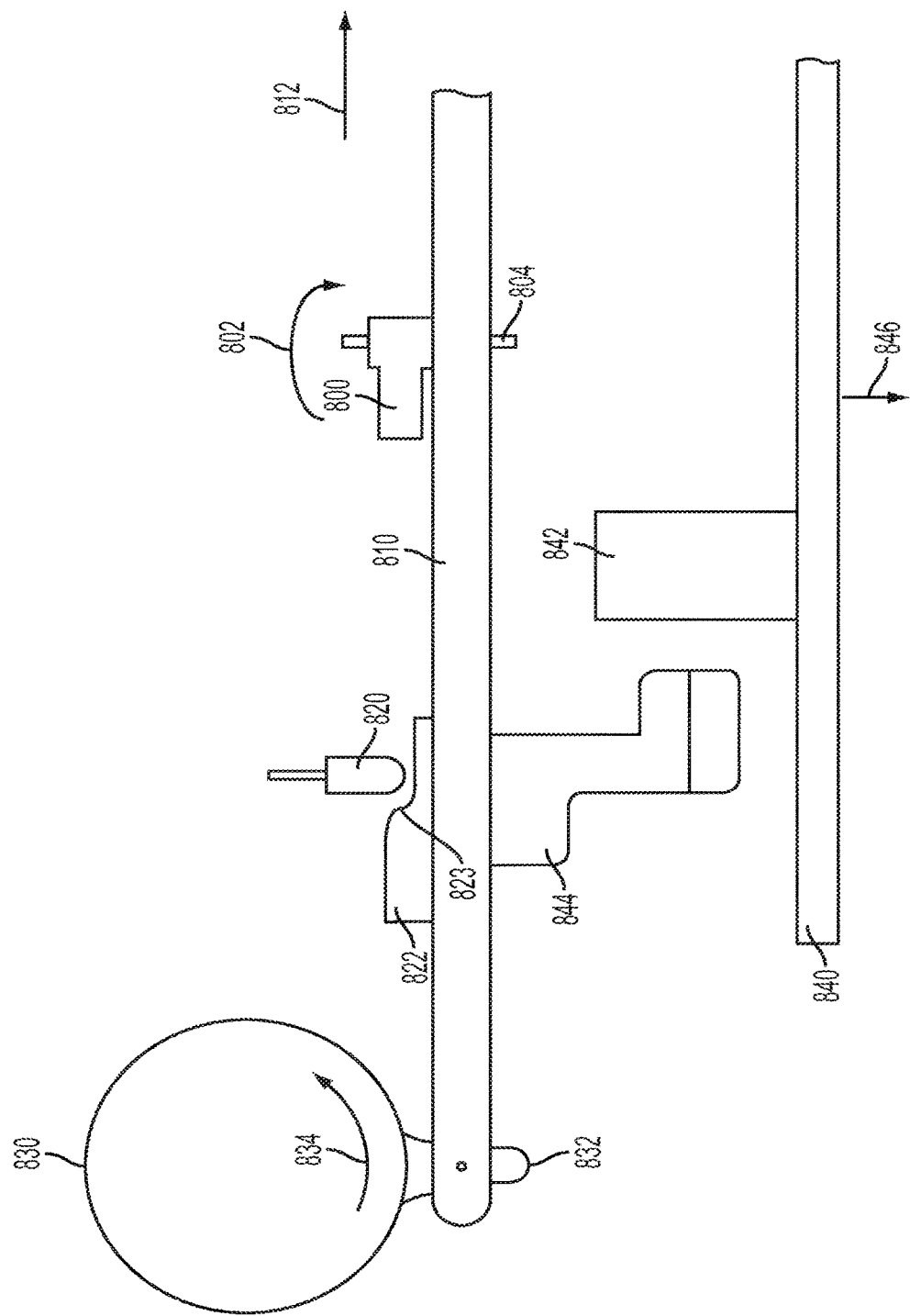
FIG. 9 depicts a schematic view of a manual release device in a first state, according to an exemplary embodiment.

It may be desirable to provide a patient side cart with a manual release device to manually retract the vibration reduction member(s) of the patient side cart, such as when a user wishes to retract the vibration reduction member(s) and quickly move the patient side cart. Turning to FIG. 9, an exemplary embodiment of a manual release system is schematically depicted. As shown in FIG. 9, a handle or lever 800 may be provided for a user to actuate and manually retract vibration reduction member(s). Although handle 800 is shown in the exemplary embodiment of FIG. 9, the various exemplary embodiments described herein may use other manual actuation devices. Handle 800 may be connected to a pin 804, for example, so that handle 800 may rotate in direction 802 about pin 804 to the position shown in FIG. 10.

Actuation of handle 800 may actuate a release valve to permit vibration reduction member(s) to be retracted. According to an exemplary embodiment, linkage 810 may be connected to handle 800 so that when handle 800 is manually actuated in direction 802, linkage 810 is moved along direction 812. According to an exemplary embodiment, linkage 810 may be connected to, or include, a cam block 822 configured to engage a release valve 820 of a hydraulic pressure system, such as release valve 420 or 520 of the exemplary embodiments of FIGS. 5 and 6. Thus, when linkage 810 is moved in direction 812, a cam surface 823 of cam block 822 may engage release valve 820, forcing release valve 820 along direction 821 in FIG. 10 to an open position, which releases the pressure in the hydraulic system and permits vibration reduction member(s) to be retracted, as described in the exemplary embodiments above.

Figure 10:
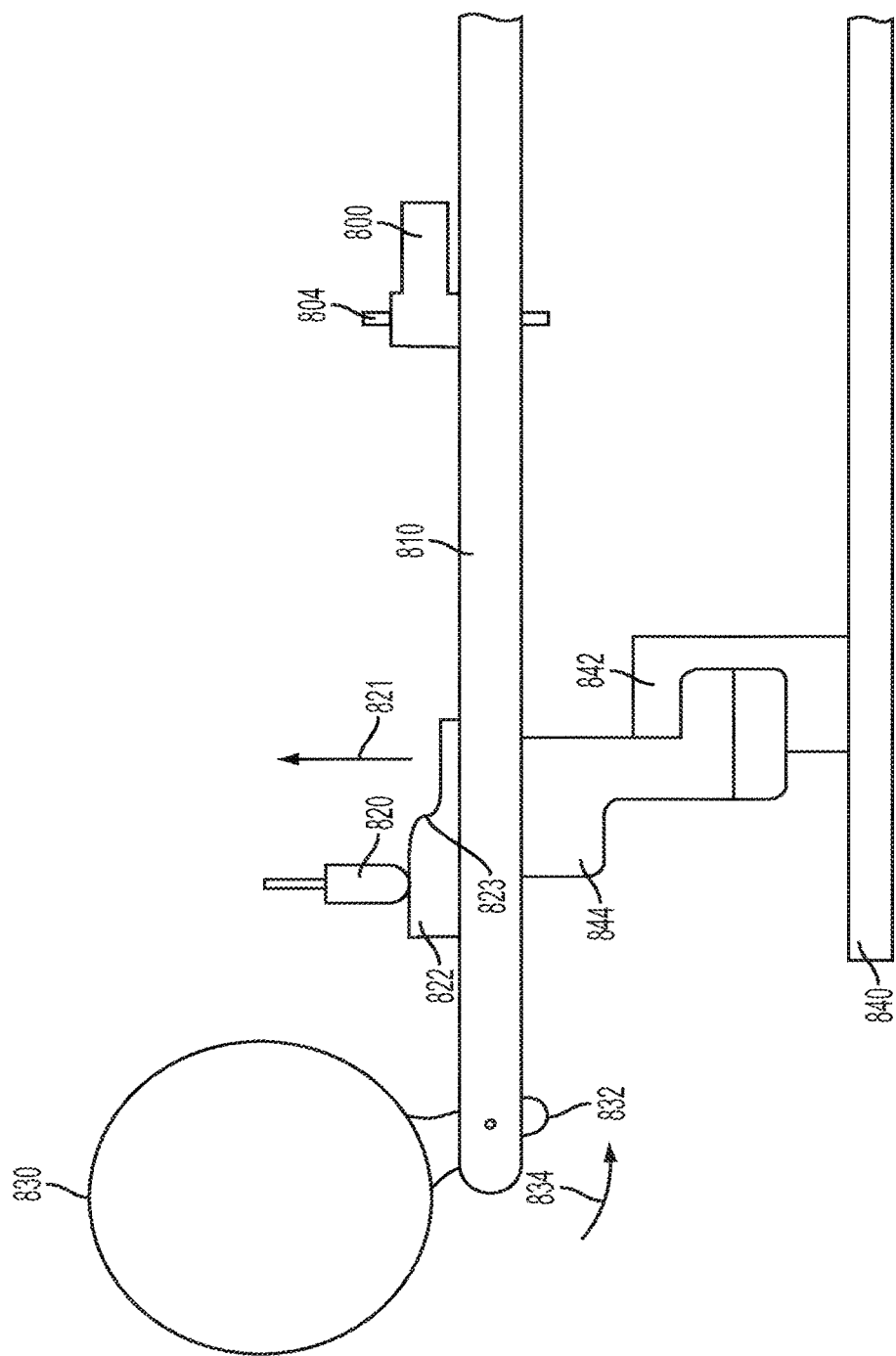
FIG. 10 depicts the manual release device of FIG. 9 in a second, actuated state.

As described above, driven wheels of a patient side cart may be immobilized when vibration reduction member(s) are deployed to facilitate immobilization of the patient side cart. Actuation of the manual release device (e.g., handle 800) may unlock the driven wheels, according to an exemplary embodiment. As depicted in FIGS. 9 and 10, linkage 810 may be connected to a member 832 of an electric motor 830 for driving a driven wheel (such as, for example, motor 211 or 213 in the exemplary embodiment of FIG. 2). Thus, when linkage 810 is moved in direction 812, member 832 and electric motor 830 may be rotated along direction 834 to a position in which electric motor 830 has been manually unlocked, permitting a driven wheel (such as, for example, wheel 210 or 212 in the exemplary embodiment of FIG. 2) associated with electric motor 830 to freely rotate. Although linkage 810 is depicted as being connected to a single electric motor 830 in the exemplary embodiment of FIGS. 9 and 10, linkage 810 may be connected to a plurality of electric motors of a patient side cart to unlock each motor and facilitate movement of the cart.

As described above in regard to the exemplary embodiment of FIGS. 9 and 10, actuation of a manual release device (e.g., handle 800) may place a patient side cart in a neutral state in which the patient side cart is free to move and vibration reduction member(s) have been retracted, such as due to the actuation of release valve. To deploy the vibration reduction member(s) once again and/or lock driven wheel(s) via electric motor(s), the manual release device may need to be returned to its initial state, such as the state of handle 800 in the exemplary embodiment of FIG. 9. However, it is possible a user may forget to return the manual release device to its initial state. Thus, it may be desirable to provide a means of notifying a user that the manual release device is in an actuated state.

Figure 12:
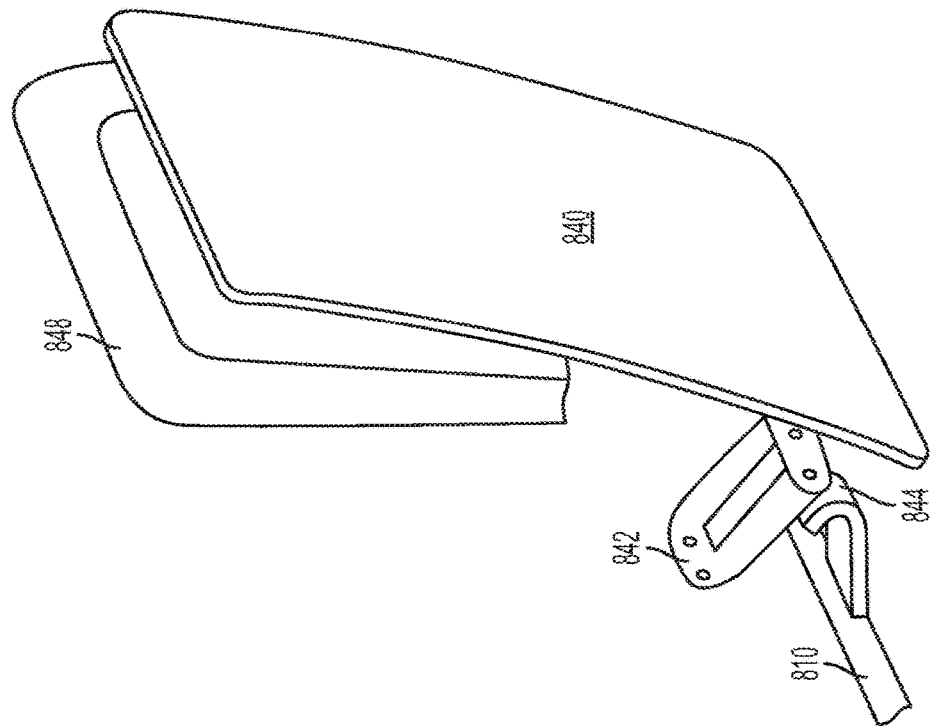
FIG. 12 depicts a partial perspective view of the manual release device of FIG. 10 and an access door in a second, actuated state.
Figure 11:
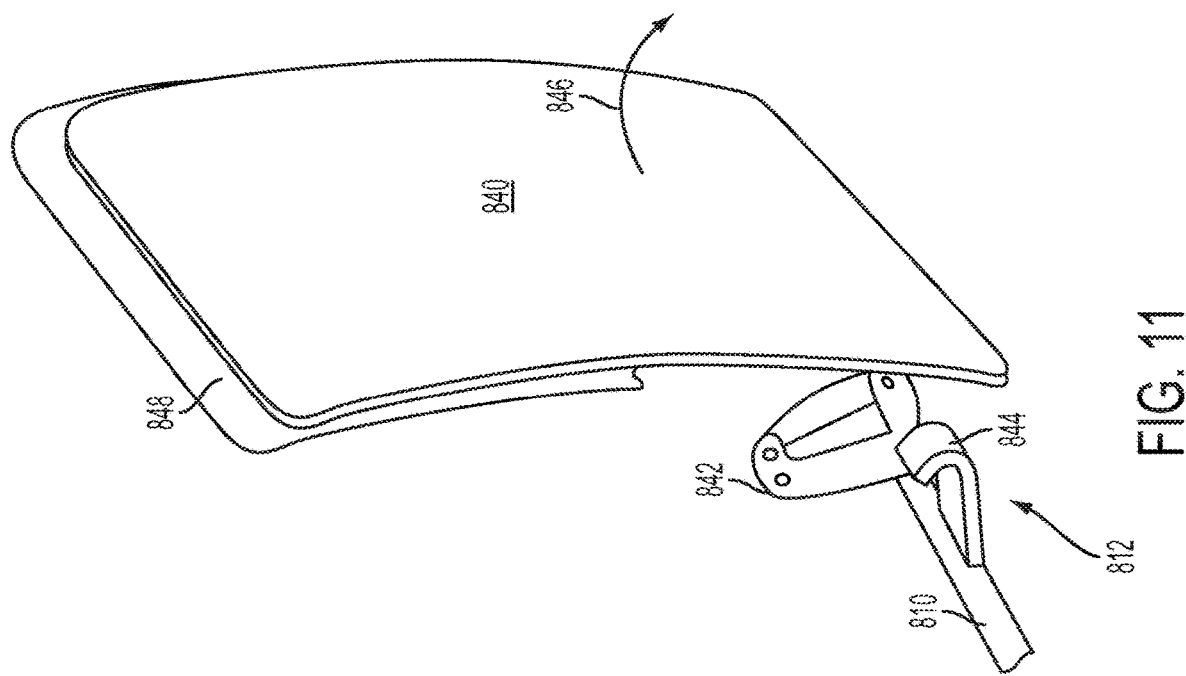
FIG. 11 depicts a partial perspective view of the manual release device of FIG. 9 and an access door in the first state.

As indicated in FIGS. 9 and 10, handle 800, linkage 810, and other devices associated with the manual release device may be housed in a compartment behind a door 840, such as within a base of a patient side cart. Door 840 may be opened by a user to access handle 800 inside of the compartment, such as by swinging door 842 open via hinge 842 in direction 846, as shown in FIG. 9 and in FIG. 11, which depicts a perspective view of door 840 in a closed state relative to a frame 848. According to an exemplary embodiment, a biasing device (not shown), such as a spring or other biasing device, may bias door 840 to an open position once door 840 has been moved from the closed position. However, once handle 800 has been actuated to move linkage 810 along direction 812, a stop member 844 connected to linkage 810 also moves along direction 812 to the position shown in FIGS. 10 and 12. When stop member 844 is in the position depicted in FIGS. 10 and 12, stop member 844 engages hinge 842 when an attempt is made to shut door 840, preventing door 840 from closing against frame 848. In this way, a user may be notified that the manual release device remains in an actuated state because the user will be unable to close the door 840 providing access to the manual release device.

Other notification devices may be used in addition to or besides the exemplary embodiment of FIGS. 9-12. According to an exemplary embodiment, a sensor may be provided to detect when a manual release device (e.g., handle 800) is in an actuated state. A signal from the sensor may be used to provide feedback, such as via visual and/or audio feedback, to user that the manual release device is in an actuated state.

Although various exemplary embodiments described below may refer to a patient side cart of a robotic surgical system, those having ordinary skill in the art would understand how to utilize the carts and vibration reduction members described herein for other wheeled platforms, such as, for example, imaging equipment, operating tables, and other wheeled devices.

Providing a patient side cart with vibration reduction member(s) facilitates reduction of vibrations occurring in the patient side cart and surgical instruments mounted to the patient side cart. The vibration reduction member(s) may be deployed or retracted relative to a ground surface to facilitate reduction of the vibrations and movement of the patient side cart. Further, the patient side cart may include a controller to control deployment and retraction of the vibration reduction member(s) to facilitate automatic deployment and retraction of the vibration reduction member(s) without requiring commands from a user.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A surgical cart assembly, comprising:
    a base portion;
    a plurality of wheels coupled to the base portion, the plurality of wheels being configured to permit wheeled movement of the surgical cart assembly;
    a column extending vertically from the base portion;
    a manipulator arm coupled to an end portion of the column opposite to a location of the base portion;
    a stabilization device coupled to the base portion, the stabilization device moveable between a retracted position and a deployed position;
    an actuation device configured to cause movement of the stabilization device between the retracted position and the deployed position in response to actuation of the actuation device; and
    a biasing element coupled to the stabilization device, the biasing element exerting a biasing force to bias the stabilization device towards the retracted position,
    wherein the stabilization device comprises a stabilization surface, the stabilization surface contacting the ground surface on which the surgical cart assembly is supported in the deployed position of the stabilization device, and the stabilization surface spaced from the ground surface in the retracted position of the stabilization device.

2. The surgical cart assembly of claim 1, wherein the biasing element comprises a spring.

3. The surgical cart assembly of claim 2, wherein the actuation device is configured to exert a force sufficient to overcome the biasing force of the spring to move the stabilization device from the retracted position to the deployed position.

4. The surgical cart assembly of claim 1, wherein the actuation device comprises a motor.

5. The surgical cart assembly of claim 1, wherein the stabilization device in the retracted position is fully retracted relative to a bottom surface of the base portion.

6. The surgical cart assembly of claim 1, further comprising a manual release device operably coupled to the stabilization device to manually move the stabilization device from the deployed position to the retracted position.

7. The surgical cart assembly of claim 1, further comprising a cam surface, movement of the cam surface causing the stabilization device to move from the deployed position to the retracted position.

8. The surgical cart assembly of claim 1, further comprising a plurality of a stabilization devices coupled to the base portion, the stabilization device being one of the plurality of stabilization devices, each of the plurality of stabilization devices moveable between the retracted position and the deployed position.

9. The surgical cart assembly of claim 8, wherein the actuation device causes movement of the plurality of stabilization devices between the retracted position and the deployed position in response to actuation of the actuation device.

10. The surgical cart assembly of claim 8, further comprising a plurality of actuation devices respectively coupled to the plurality of a stabilization devices, the actuation device being one of the plurality of actuation devices, each of the plurality of actuation devices causing movement of a corresponding one of the plurality of stabilization devices between the retracted position and the deployed position in response to actuation of the actuation device.

11. The surgical cart assembly of claim 1, wherein the plurality of wheels comprises one or more motorized wheels.

12. The surgical cart assembly of claim 1, wherein the plurality of wheels comprises one or more non-motorized wheels.

13. The surgical cart assembly of claim 1, wherein the plurality of wheels are in contact with the ground surface in the deployed position of the stabilization device.

14. The surgical cart assembly of claim 1, wherein in the deployed position of the stabilization device, the wheeled movement of the surgical cart assembly is locked to immobilize the surgical cart assembly.

15. A system for controlling stability of a wheeled platform, the system comprising:
    a base;
    wheels coupled to the base;
    one or more stabilization devices movable between deployed and retracted positions relative to the base, wherein the one or more stabilization devices are in contact with the ground surface in the deployed positions and not in contact with the ground surface in the retracted positions; and
    an actuation device configured to automatically deploy the one or more stabilization devices to the deployed positions in response to being placed in a first operational mode,
    wherein the wheeled platform is configured to support a surgical instrument during a surgical procedure.

16. The system of claim 15, further comprising a controller configured to determine that the wheeled platform is in a first configuration and to output a control command to place the actuation device into the first operational mode to cause the actuation device to automatically deploy the one or more stabilization devices to the deployed positions.

17. The system of claim 16, wherein the first configuration corresponds to preparation of the wheeled platform for a surgical procedure.

18. The system of claim 15, further comprising one or more biasing elements respectively coupled to the one or more stabilization devices, the one or more biasing elements exerting a biasing force to bias the one or more stabilization devices towards the retracted position.

19. The system of claim 18, wherein the one or more biasing elements comprise one or more springs.

20. The system of claim 15, further comprising
a plurality of stabilization devices, including the one or more stabilization devices; and
a plurality of actuation devices, including the actuation device, each actuation device operably coupled to a respective one of the plurality of stabilization devices to cause individual movement of the stabilization devices between the retracted position and the deployed position.

\* \* \* \* \*